(12) United States Patent
Bukowski

(10) Patent No.: US 6,588,670 B2
(45) Date of Patent: Jul. 8, 2003

(54) MEDICAL DIAGNOSTIC MONITORING

(75) Inventor: Brian Bukowski, Farmingville, NY (US)

(73) Assignee: Symbol Technologies, Inc., Holtsville, NY (US)

( * ) Notice: Subject to any disclaimer, the term of this patent is extended or adjusted under 35 U.S.C. 154(b) by 0 days.

(21) Appl. No.: 10/021,345

(22) Filed: Dec. 7, 2001

(65) Prior Publication Data

US 2003/0106940 A1 Jun. 12, 2003

Related U.S. Application Data

(60) Provisional application No. 60/339,080, filed on Oct. 30, 2001.

(51) Int. Cl.⁷ ................................................. G06K 7/10
(52) U.S. Cl. .................................. 235/462.45; 235/375
(58) Field of Search ................................ 235/375, 380, 235/381, 383, 462.01, 462.02, 472.01–472.03, 494, 462.45, 462.25

(56) References Cited

U.S. PATENT DOCUMENTS 6,171,237 B1 * 1/2001 Avitall et al. ............... 600/300
6,221,012 B1 * 4/2001 Maschke et al. ............ 600/301
2002/0099274 A1 * 7/2002 Isomura et al. ............. 600/300

OTHER PUBLICATIONS

Accu–Chek Simplicity User's Manual, Copyright 2000 Roche Diagnostics.

* cited by examiner

*Primary Examiner*—Thien M. Le
(74) *Attorney, Agent, or Firm*—Carter, Deluca, Farrell & Scmhmidt

(57) ABSTRACT

An apparatus and system for providing improved monitoring of diagnostic results of a user. The apparatus includes a diagnostic monitor that allows patients to easily, quickly and reliably enter information about daily health activity. Specifically, the apparatus has an integrated or removable secured reader for reading coded health related information. The reader may be a barcode scanner or imager. The user of the apparatus may use the apparatus to read coded information related to ingesting of food, taking medication, exercising, sleeping, experiencing stress related events, etc.

25 Claims, 8 Drawing Sheets

MEDICAL DIAGNOSTIC MONITORING

RELATED APPLICATION

This application claims the benefit of the filing date of provisional application No. 60/339,080 filed on Oct. 30, 2001, entitled "Medical Diagnostic Monitoring."

FIELD OF THE INVENTION

The present invention generally relates to medical diagnostic monitoring devices and methods of using the same. In particular, the present invention relates to a medical monitoring device having a reader for reading coded health related information.

BACKGROUND OF THE INVENTION

Portable medical diagnostic monitors are becoming more and more common as technology improves. A portable diagnostic monitor collects clinical information on or from a patient when he is out of the doctor's office carrying on with his daily routines. To better diagnose and manage certain medical conditions, it is important to track a patient's activities and match it to a diagnostic result such as but not limited to, a blood sugar reading from a portable diabetes monitor. Currently a patient either does not record his daily activities or writes his activities down on paper. Writing the information down is time consuming and prone to error. In some cases, certain portable diagnostic device may allow for limited key stroke/character entry.

Since it is important to keep the diagnostic monitor within a convenient size there is limited area on the device to provide input keys. Thus making inputting data cumbersome and time consuming. Additionally, many users of the diagnostic monitors may not be comfortable navigating through a series of menu displays in order to enter information on an electronic device. Other users may have difficulty reading the information on the limited display area or may have arthritic conditions that make it difficult or impossible to manipulate a series of keys on an electronic device. Thus, a need exists to provide a portable diagnostic monitor that allows patients to easily, quickly and reliably enter information about daily health activity.

SUMMARY OF THE INVENTION

The proposed invention would allow a patient to easily track and match his daily activities to the clinical information being collected by the diagnostic device. A preferred embodiment of the present invention enables a person to easily track daily activities via barcode input.

The basic components of a preferred embodiment of the present invention are a portable medical diagnostic device and a miniature identification capture reader. The identification capture reader could be a barcode scanner, imager, infrared identification reader or similar technology.

The subcomponents of the medical device may be a battery, display, keyboard, cradle, wireless communications circuitry, memory, housing, central processing unit (CPU) and telephony components. The medical device could be any portable diagnostic monitor that patients would carry around to monitor a specific vital health sign. For instance, the device may include, but not limited to, the following monitors: heart rate monitor, blood pressure monitor, cholesterol monitor and diabetes monitor. The portable diagnostic device could be portable digital assistance ("PDA") or notebook computer that includes a module and/or software for monitoring a user's health signs. The barcode scanner could be integrated into the medical diagnostic device or attached to the medical diagnostic device via an accessory device. The barcode scanner could be formed as a sled type device that can be removably secured to the medical diagnostic device.

Along with carrying the portable diagnostic device, which may have a barcode scanner attached or integrated inside, a patient would also carry a small index or business sized cards with pre-printed 1D or 2D barcodes that relate to a specific health related activity. The health related activities could be eating certain types of food, eating certain amounts of food, taking medications, exercising, sleeping, experiencing stress related events, etc. In a preferred embodiment, meals could be available that include a barcode that includes specific health information to be registered with the portable diagnostic device of the present invention. For example, a line of frozen dinners could have a two-dimensional barcode that provides information about the food. In addition, to identifying the ingredients, the barcode could contain information about the amount of sugar, fat and cholesterol per serving. Similarly, restaurants could provide the barcodes for the food the customer ordered on menus or other printed sheets of paper.

Before or after one of the health related activities occur, the patient scans with the portable diagnostic device of the present invention a particular barcode associated with the activity. Barcode scanning allows for a quick and error proof way to enter and record the data. By comparing the clinical results from the diagnostic monitor to activities entered by the barcode scanner the patient and the doctor can provide a better and a more complete diagnosis. All the data would be stored in the monitor and/or sent over a wireless or wired connection to a database.

An object of the present invention is to provide a portable diagnostic device having a reader integrated therein which allows a patient to record accurately and easily daily health activity.

Another object of the present invention is to provide a portable diagnostic device accessory having an integrated scanner which can be removably secured to a portable diagnostic device, the combination allows a patient to record accurately and easily daily health activity.

A still further object of the present invention is to provide printed barcode labels that may be used with a portable diagnostic device for accurately and easily recording daily health activity.

A still further object of the present invention is to provide a portable diagnostic device that can be calibrated easily by scanning a calibration barcode.

DETAILED DESCRIPTION OF THE INVENTION

Figure 1:
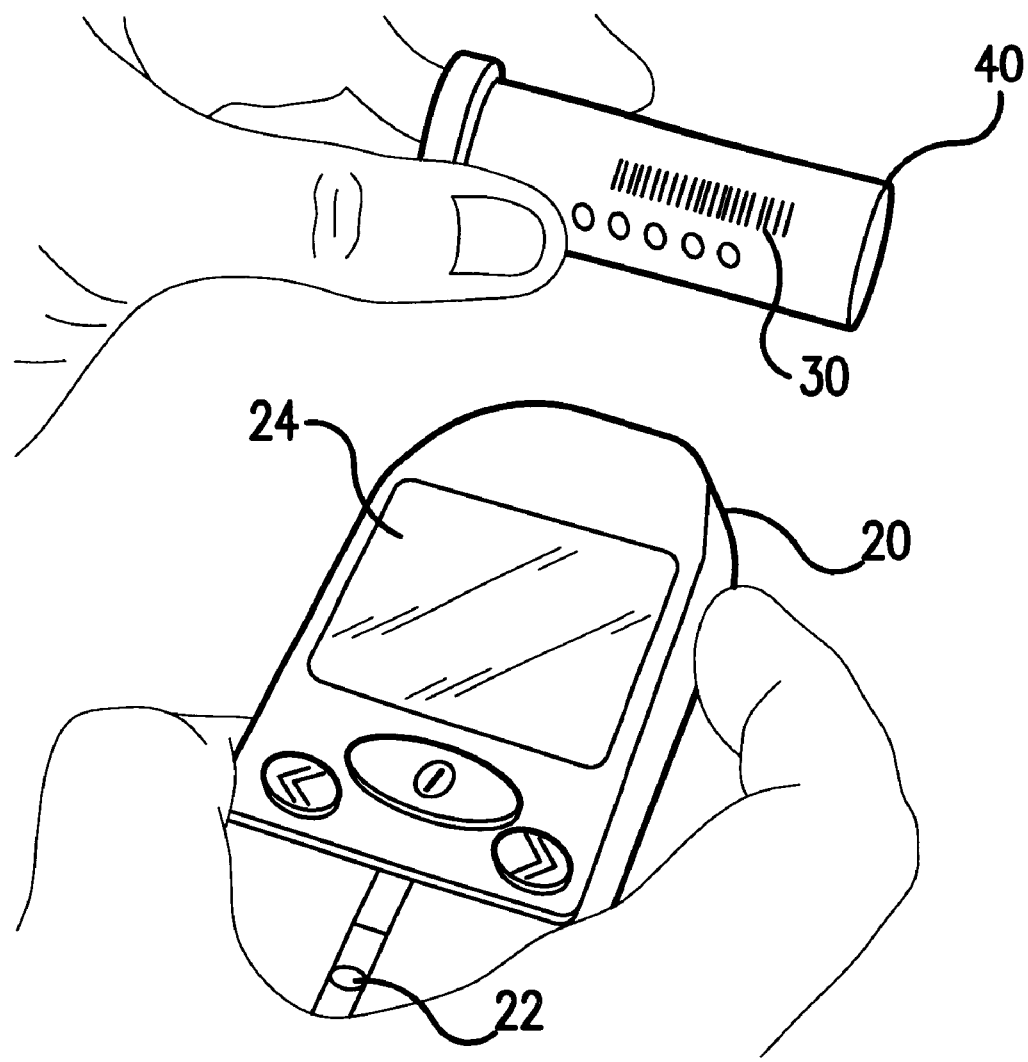
FIG. 1 is a preferred embodiment of the present invention being used to scan a barcode on a drug canister.

The present invention will now be described with reference to the drawings, wherein like reference numerals are used to refer to like elements throughout.

Figure 2:
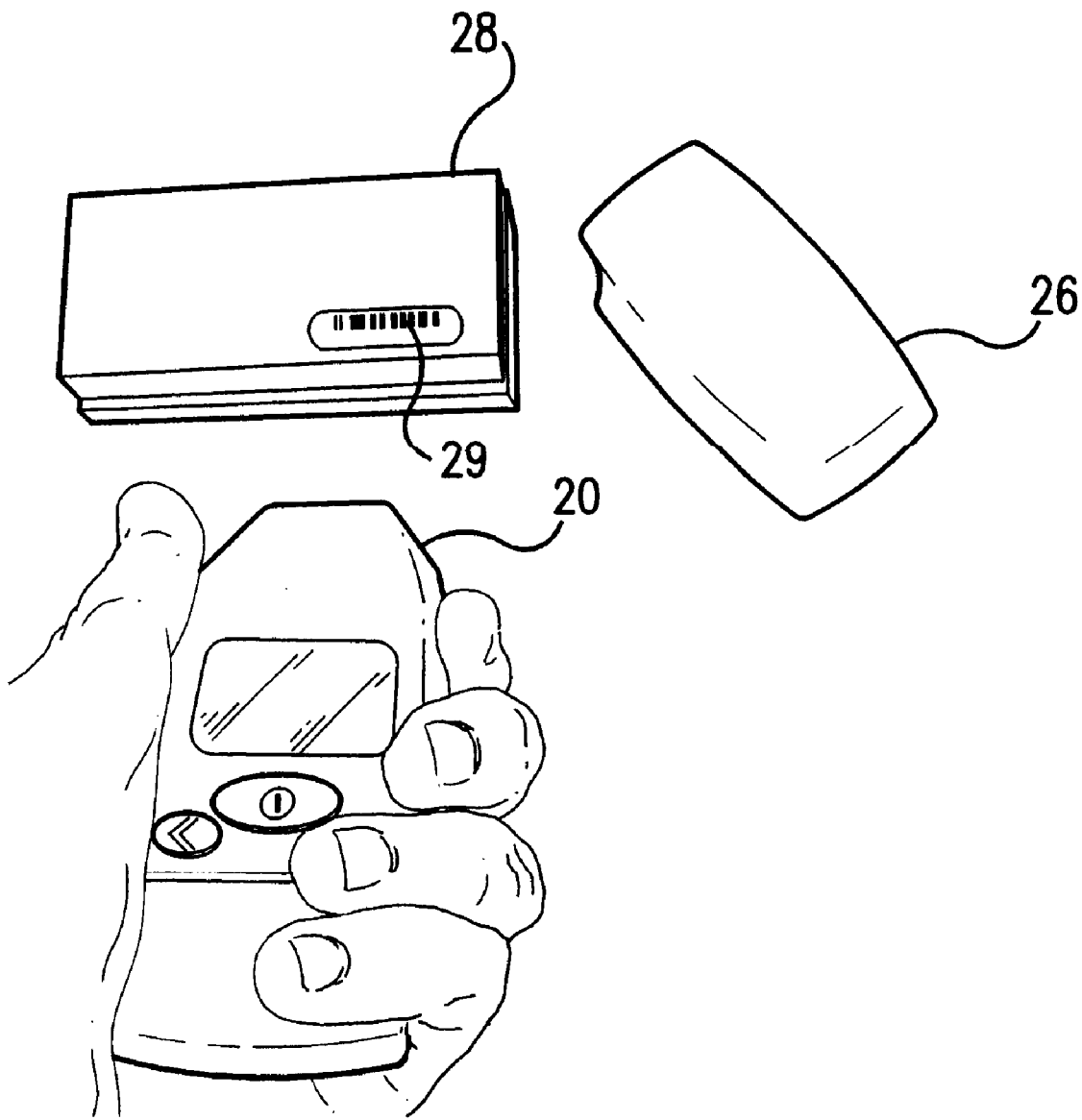
FIG. 2 is the embodiment shown in FIG. 1 being used to scan a calibration barcode.

Referring to FIGS. 1 and 2, a preferred embodiment of a portable diagnostic device 20 is shown. In this embodiment of the invention, portable diagnostic device 20 is a device used by patients that have diabetes. The term "patient" is used herein to describe a person who uses a portable diagnostic device to periodically monitor his or her health signs. Portable diagnostic device 20 includes a meter 22 for reading a patient's blood glucose level. The patient tests his or her blood glucose level by placing over meter 22 a test strip that has a sample of the patient's blood. The results of the test can be displayed to the user on display 24. Portable diagnostic device 20 also includes internal memory for recording the results as well as the date and time. A carrying case 26 may be provided for storing portable diagnostic device 20 when it is not being used.

Figure 1A:
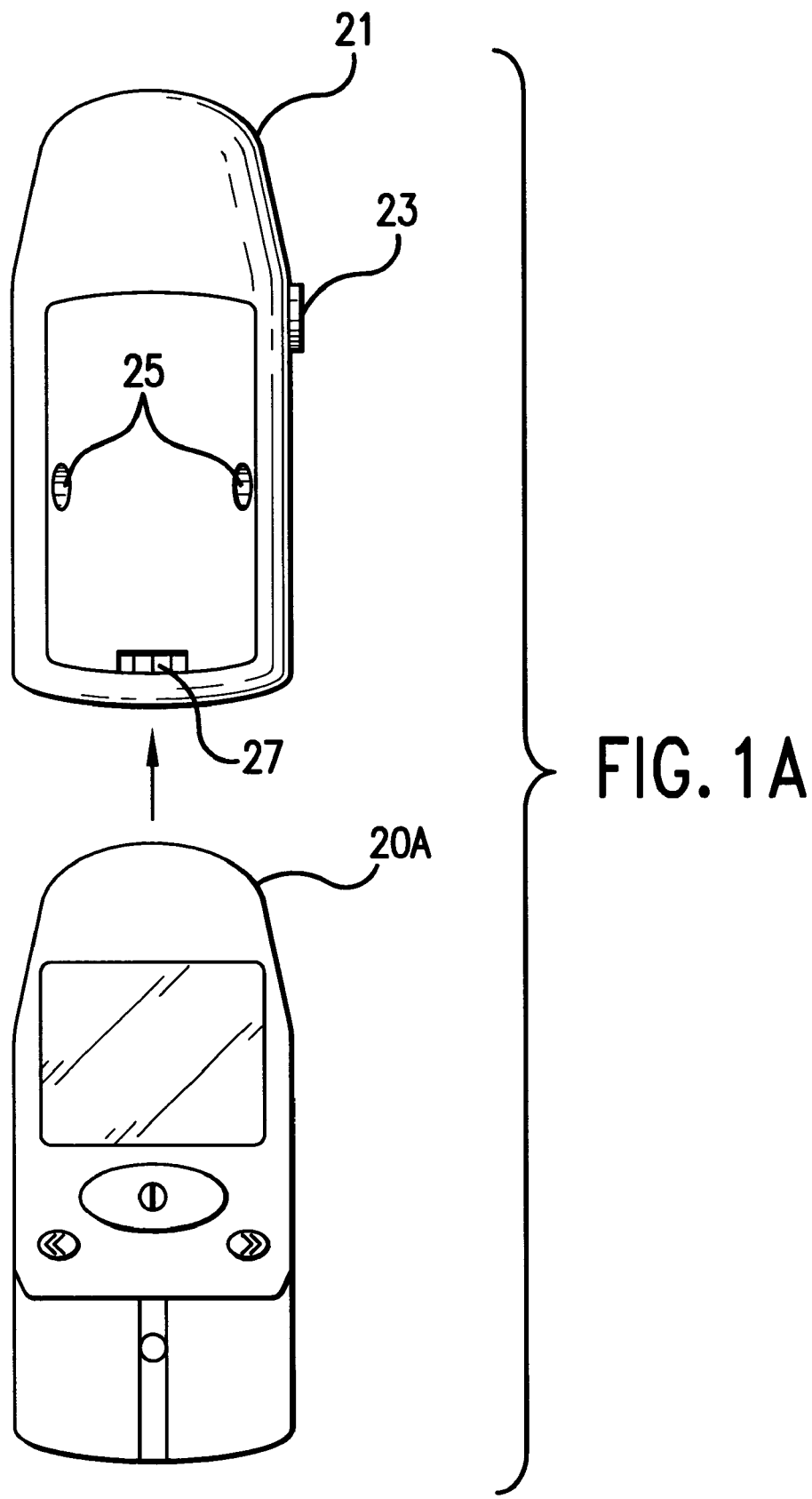
FIG. 1A is another embodiment of the present invention having a removably secured sled accessory.

FIG. 1A shows an alternative embodiment of the present invention. A portable diagnostic device 20A can be secured to a sled accessory 21 that contains an integrated barcode scanner. Sled accessory 21 contains latching mechanisms 25 that allow a user to removably secure sled accessory 21 to portable diagnostic device 20A. When the two components are secured together, a communications port 27 on sled accessory 21 engages with a similar port on the back of portable diagnostic device 20A (not shown). Thus, data and information can be transferred between the two components. Sled accessory also has a trigger 23 for activating the scanning function.

In addition to measuring a patient's blood glucose level, portable diagnostic device 20 is able to input data via a barcode scanner. The data may include information about the patient's health related activities. Portable diagnostic device 20 includes an integrated scanner for scanning a barcode 30 to input health related activity data. Portable diagnostic device 20 includes a trigger for activating the scanner. In FIG. 1, barcode 30 is associated with a prescription drug stored within a canister 40. Thus, barcode 30 may include data relating to the prescription drug being taken by the patient. Thus, after a patient takes a does of the drug, he scans barcode 30 with portable diagnostic device 20. Portable diagnostic device 20 records at least part of the data stored in barcode 30. Portable diagnostic device 20 may also record a date/time stamp to provide a record of the approximate time the patient took the drug. Alternatively, the patient could input a different time representing when he took the drug. The portable diagnostic device 20 may also record the dosage of the drug taken by the patient. A single scan of barcode 30 could represent a patient's normal drug dosage. Alternatively, a scan could represent one pill. Thus, if a patient takes two pills from canister 40, he would scan barcode 30 two times. After a successful scan, portable diagnostic device 20 could display on display 24 the drug taken by the patient, the dosage and the time of consumption.

Portable diagnostic device 20 could store a patient's prescription drug schedule. The prescription drug schedule provides information about what prescription drugs the patient is supposed to take and when the patient should take them. The prescription drug table may be entered by the patient or downloaded from a computer associated with a doctor or pharmacist. Thus, portable diagnostic device 20 could provide a reminder to the patient to take a certain prescription drug upon a triggering event. The triggering event could be the time of day, the user's ingesting of food, the user's monitored daily activity, etc. Portable diagnostic device 20 could also help prevent the patient from taking a drug at an inappropriate time. After the patient scans a canister of the drug he is about to take, portable diagnostic device 20 compares the information from the barcode to the prescription drug schedule. Portable diagnostic device 20 could provide a warning (audible and/or visual) to the patient if a) the scanned drug is not one prescribed to the patient, b) the scanned drug would conflict with a previously scanned prescription drug taken by the patient, c) it is not the proper time of the day for the patient to be taking the drug, d) the patient has not eaten enough food (as determined by codes previously scanned by the user), or e) the patient would be exceeding the proper dosage. If the patient has improperly taken a drug, portable diagnostic device 20 could provide precautionary instructions could be provided to the patient. For instance, portable diagnostic device 20 may display a message that the patient should contact has doctor immediately. Portable diagnostic device 20 may also automatically send a notification to a doctor, guardian or emergency personnel of the patient's activity. The notification could be sent via a wireless communications circuitry within portable diagnostic device 20.

Figure 3:
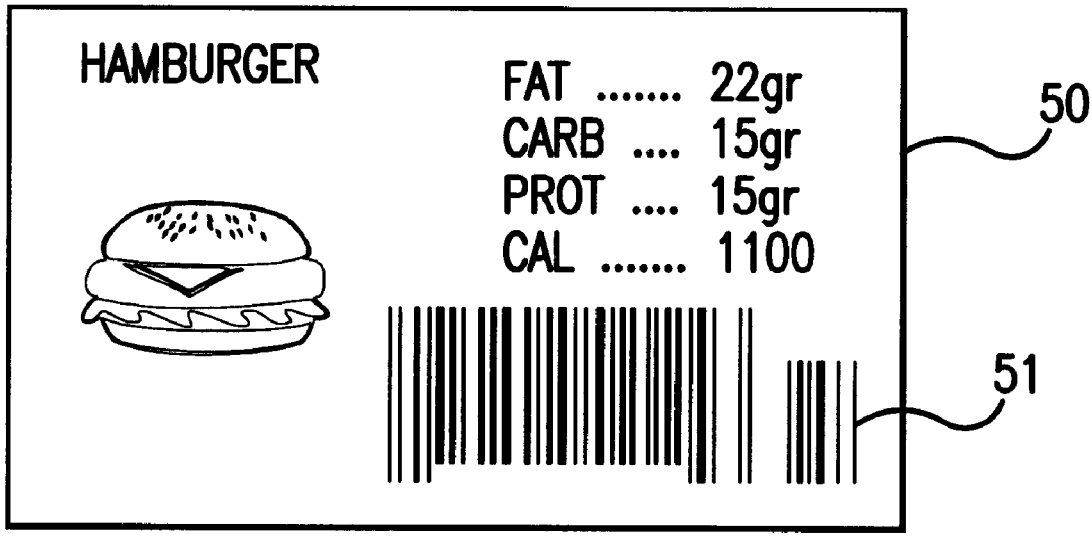
FIG. 3 shows two cards containing information relating to food that may be used to input data into the portable diagnostic device of the present invention.
Figure 3:
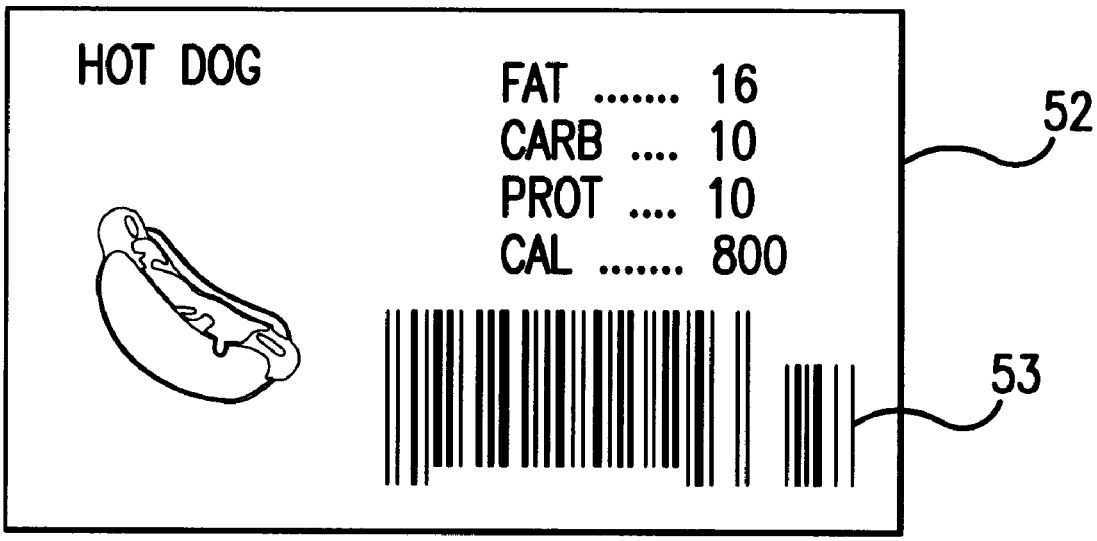

FIG. 3 shows two cards 50 and 52 that may be used in conjunction with portable diagnostic device 20. The cards contain human recognizable information and a two-dimensional barcode 51 and 53. The human recognizable information may include a type of food and nutritional information about the food. The nutritional information may include the amount fat, protein, carbohydrates (complex and simple), calories, vitamins, nutrients, additives, etc. Barcodes 51 and 53 contain information that needs to be monitored by the patient. For instance, barcodes 51 and 53 may include all or some of the nutritional information listed above. Barcodes 51 and 53 may also include information about all of the ingredients in the food.

In a preferred embodiment of the present invention, a patient would have available a plurality of cards similar to those shown in FIG. 3. After (or before) a patient eats a certain food, the patient would scan with portable diagnostic device 20 a barcode on a card that represents the type of food eaten by the patient. A single scan could represent one serving of the food. If the patient has multiple servings of the food, he could scan the card multiple times. Alternatively, the card could include a barcode that represents the number of servings eaten by the patient to be scanned by the patient or the patient could manually enter the number of servings he has eaten. Portable diagnostic device 20 may record the date and time of the approximate time the patient ate the food. Alternatively, the patient could input a different time representing when he ate the food. In another embodiment, the patient could scan one of the cards right before he begins to eat a meal and then scan the card a second time when he completes his meal. Portable diagnostic device 20 could record (and display) the elapsed time the patient eats his meal.

Before the patient eats, portable diagnostic device 20 may analyze the information provided on the food to determine whether the patient should eat the food. If the food is determined to be something that the patient should not eat, a warning may be provided to the patient. The warning could be written on display 24 or it could be an audible warning. Portable diagnostic device 20 may determine that the patient should avoid a certain food by comparing the food to be eaten to a database of foods to be avoided. The database may be stored locally on portable diagnostic device 20 or at a remote location. The database of foods to be avoided could be derived from those that are known in the scientific community to be problematic, e.g., junk food. Additionally, the database of foods to be avoided could be derived from the patient's personal responses to certain foods. For instance, by analyzing a patient's diagnostic monitoring results and the foods the patient has eaten, portable diagnostic device 20 (or a remote computer that downloads the information stored on portable diagnostic device 20) could determine that certain foods are problematic to the patient. If the patient scans a barcode indicating that the patient is about to eat a food that has shown to be problematic, a warning could be displayed to the patient reminding him of the results of previous times the patient ate the food. In another embodiment, after a patient scans a barcode associated with a piece of cake he is considering eating, portable diagnostic device 20 could display how much sugar is in the cake.

Figure 6:
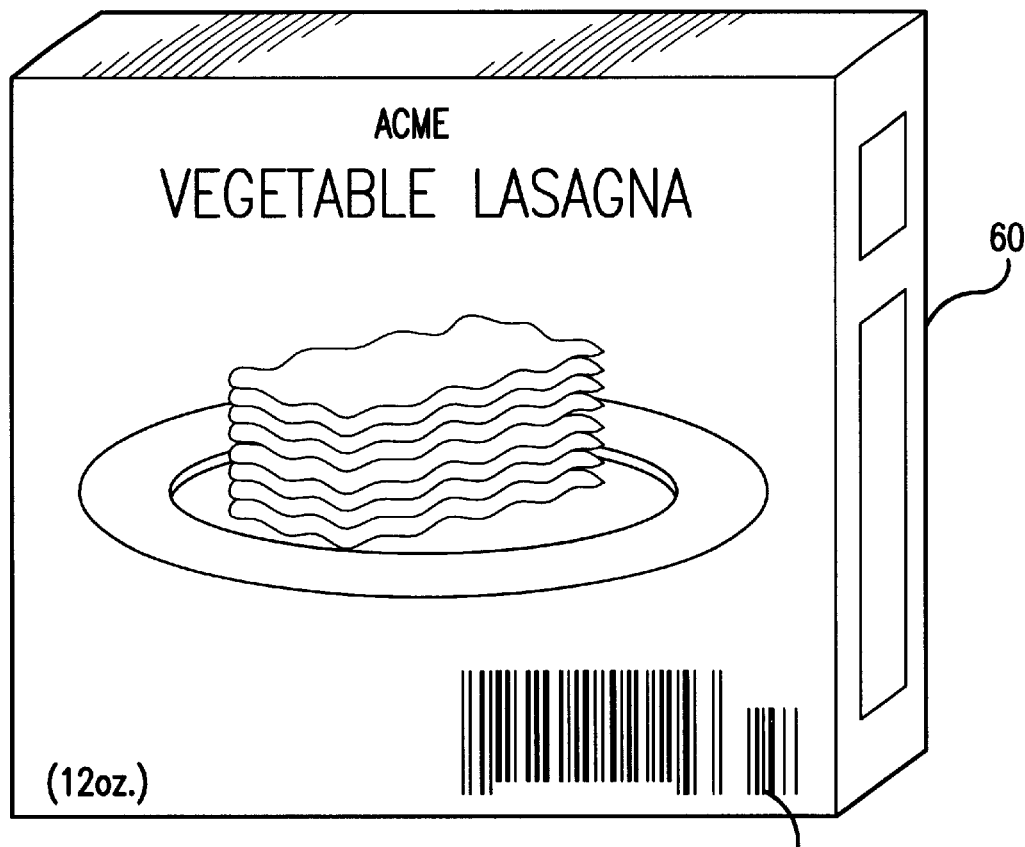
FIG. 6 shows a carton of a prepared meal that contains a two-dimensional barcode used to input data into the portable diagnostic device of the present invention.

FIG. 6 shows a two-dimensional barcode 61 on a carton 60 of a prepared meal that may be used in conjunction with portable diagnostic device 20. The prepared meal could be a single item of food, e.g., lasagna, or it could be a complete meal, e.g., chicken with rice and peas. Two-dimensional barcode 61 contains the necessary health information that needs to be monitored by the patient and recorded by portable diagnostic device 20.

Figure 7:
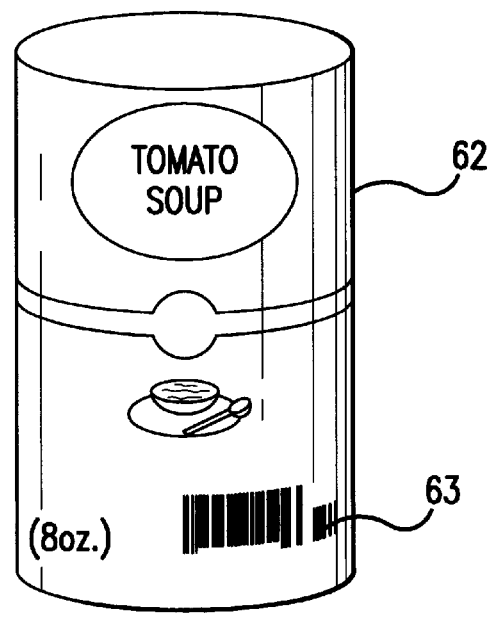
FIG. 7 shows a can of food that contains a one-dimensional barcode used to input data into the portable diagnostic device of the present invention.

FIG. 7 shows a one-dimensional barcode 63 on a can 62 of food. Barcode 63 may be a universal product code (UPC) or other identification code that uniquely identifies the food. Barcode 63 does not contain all of the information that the patient needs to monitor, but it contains an identification code that can be used to access the information from a nutritional information database. In one embodiment of the present invention, portable diagnostic device 20 includes a memory that stores the database that contains identification codes and the corresponding nutritional information for the identification codes. In another embodiment, the database is located at a remote location. Portable diagnostic device 20 could have a radio that enables a wireless link to the database or a batch connection for a hard wire link to the database. In another embodiment, portable diagnostic device 20 could transmit the identification codes entered by the scanner to a remote computing device that has access to the nutritional information database. The remote computing device could be a home computer associated with the patient or a third party that monitors the patient's daily activity. In another embodiment, a combination of these approaches could be employed. For instance, since portable diagnostic device 20 has limited memory available, it could store only the nutritional information for foods previously or frequently eaten by the patient. The information for other foods could be obtained from a remote source.

Figure 4:
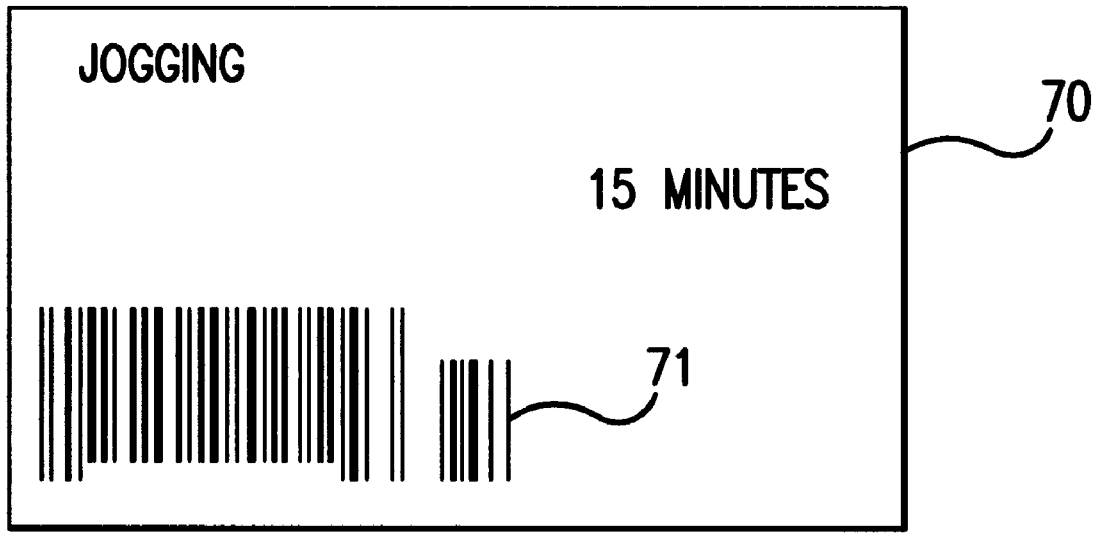
FIG. 4 shows two cards containing information relating to an activity and time period that may be used to input data into the portable diagnostic device of the present invention.
Figure 4:
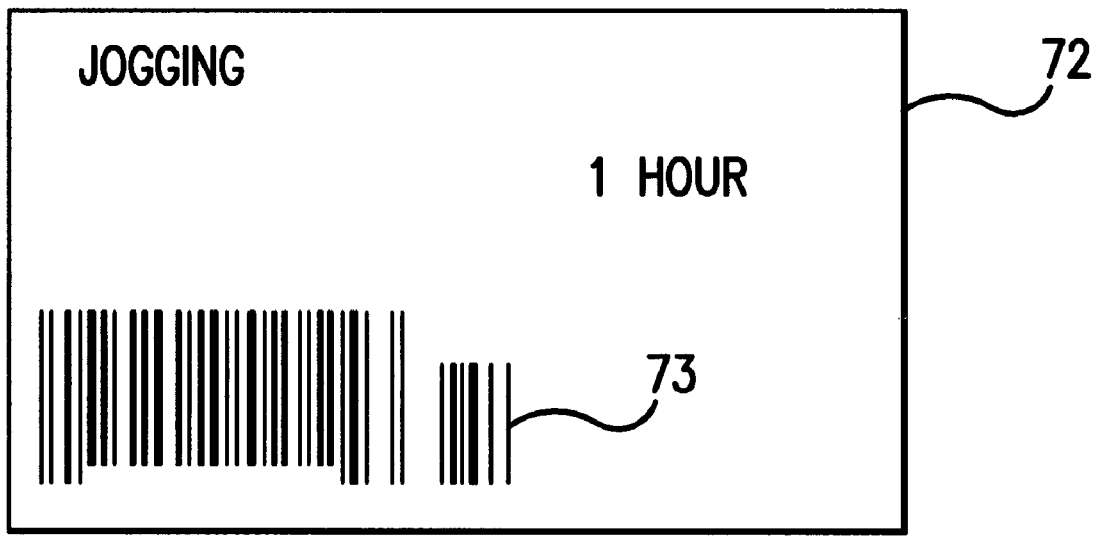

FIG. 4 shows two cards 70 and 72 that may be used in conjunction with portable diagnostic device 20. The cards contain human recognizable information and a 2 dimensional barcode 71 and 73. The human recognizable information may include an activity and a unit of time. Barcodes 71 and 73 contain information that needs to be monitored by the patient. For instance, the barcodes may include information about a type of activity and the amount of time spent doing the activity. After (or before) a patient engages in a certain activity, the patient would scan with portable diagnostic device 20 a barcode on a card that represents the activity engaged by the patient. A patient that has jogged for 15 minutes would scan card 70. A patient that has jogged for 1 hour would scan card 72. If the patient jogged for a half hour, he could scan card 70 two times. If the patient jogged for an hour and 15 minutes, he could scan card 70 once and card 72 once.

Figure 5:
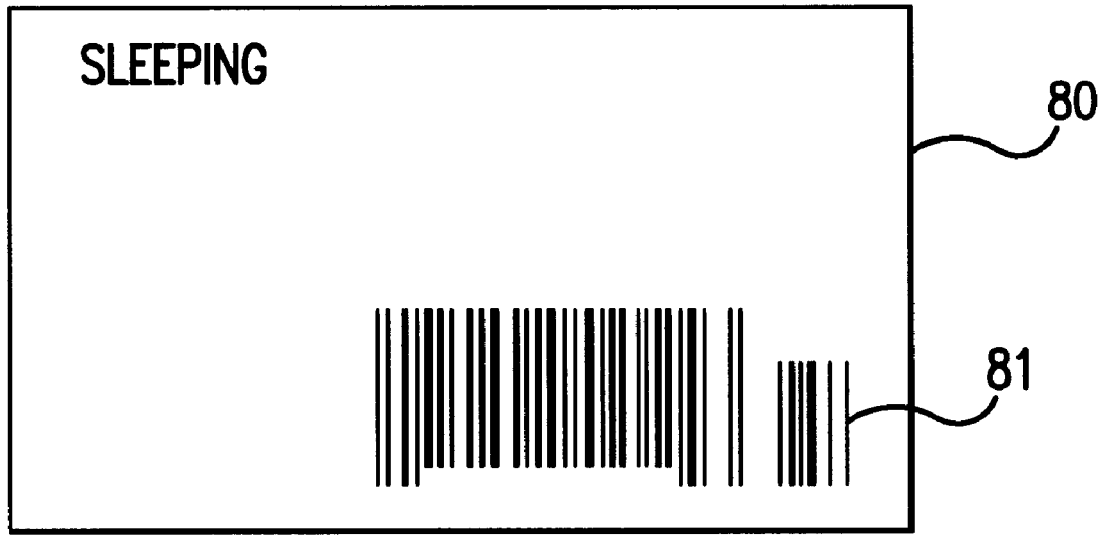
FIG. 5 shows two cards containing information about other activities that may be used to input data into the portable diagnostic device of the present invention.
Figure 5:
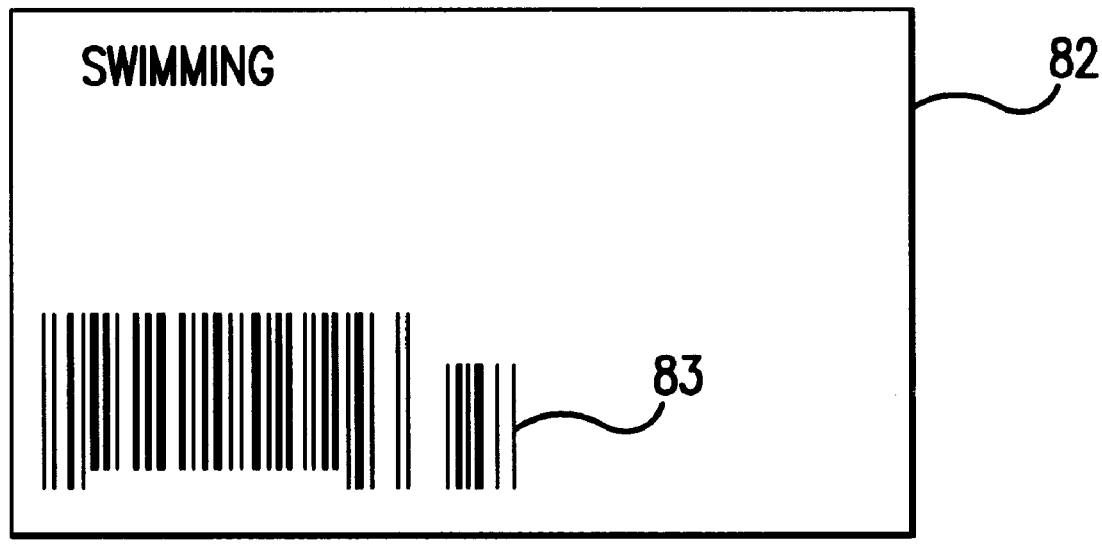

FIG. 5 shows two cards 80 and 82 that may be used in conjunction with portable diagnostic device 20. Cards 80 and 82 contain barcodes 81 and 83, respectively, that contain information that needs to be monitored by the patient. These barcodes may include only information about a type of activity engaged by the patient. For instance, barcode 81 represents sleeping and barcode 83 represents swimming. A patient who is about to start swimming uses portable diagnostic device 20 to scan barcode 83 on card 82. Portable diagnostic device 20 records the time the patient begins the activity. The patient scans barcode 83 on card 82 a second time when he completes his swimming laps. Portable diagnostic device 20 could calculate the total amount of time the patient engages in the activity. While the patient is swimming display 24 could display "Swimming" and the elapsed time spent swimming. The patient could also enter into portable diagnostic device 20 (either manually or via scanning a barcode) the number of laps during the swimming exercise.

Figure 8:
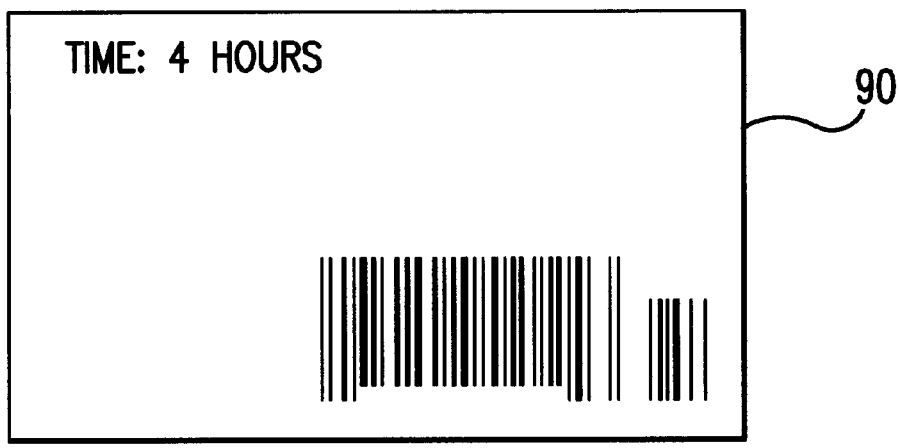
FIG. 8 shows other cards that may be used to input data into the portable diagnostic device of the present invention.
Figure 8:
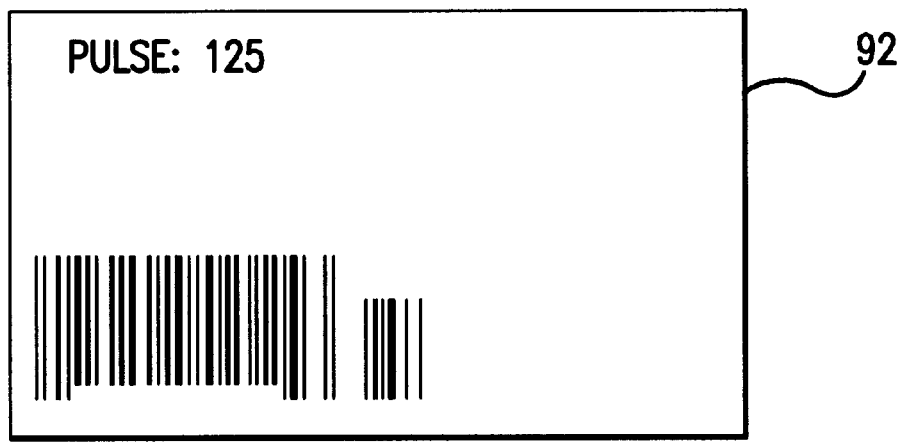
Figure 8:
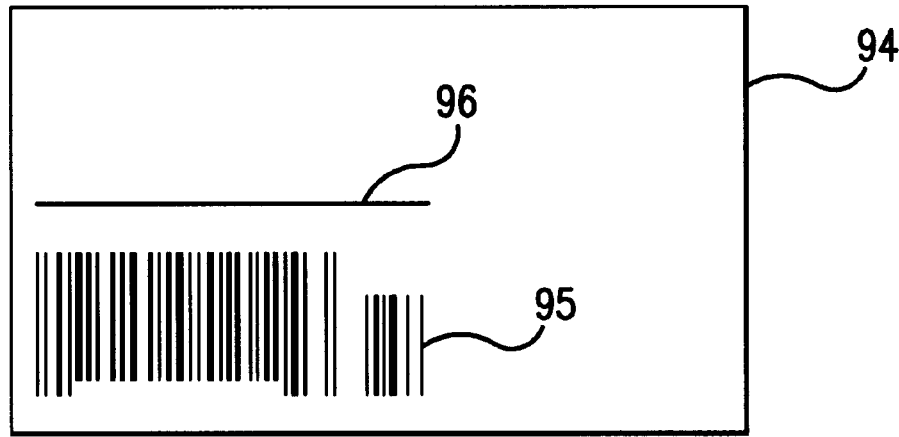

FIG. 8 shows additional cards that could be used in conjunction with portable diagnostic device 20. Card 90 provides information about a unit of time. An alternative way for a patient to provide information about an activity is to scan a card representing a certain activity, e.g., biking, and than scanning a second card, i.e., one similar to card 90 representing the amount of time engaged in the activity. The patient could employ multiple cards containing various time intervals. Card 92 provides information about a patient's pulse.

Card 94 contains a barcode 95 that can be for a user-defined activity. A user could program portable diagnostic device 20 so that barcode 95 on card 94 represents a particular exercise, food, stress related event, medications, etc. For instance, if a patient enjoys rowing, he could program portable diagnostic device 20 to recognize barcode 95 as rowing. Portable diagnostic device 20 could be set up so when the patient scans barcode 95, display 24 displays "Rowing." Card 94 contains a blank line 96. The patient could write over blank line 96 the activity programmed into portable diagnostic device 20, i.e., rowing.

Programming portable diagnostic device 20 to associate a particular activity with barcode 95 may be done as follows. The patient could set portable diagnostic device 20 to a program mode. Then the patient could scan barcode 95. Next the patient could input into portable diagnostic device 20 the specific activity. The patient could input the information via a small keypad on portable diagnostic device 20 (not shown). Alternatively, a home computer or personal digital assistant could be used to program portable diagnostic device 20. Instead of inputting information directly into portable diagnostic device 20, the information could be entered into the home computer or personal digital assistant and downloaded to portable diagnostic device 20.

In a preferred embodiment of the present invention, the scanner on portable diagnostic device 20 could be used to read information related to the performance of diagnostic monitor. In the case of diagnostic devices that measure blood glucose level by placing test strips over a meter, it is necessary to calibrate the diagnostic device for the particular lot of test strips being employed. This is customarily done today by including with the lot of test strips a small chip that contains information about the lot. This chip is inserted into the diagnostic device and read by the diagnostic device. In accordance with the principles of the present invention the information about the lot of strips could be inputted to the diagnostic device via the barcode reader. Thus, it would not be necessary to include the chip with the lot of test strips.

FIG. 2 shows a case 28 that holds a lot of testing strips. Case 28 includes a calibration barcode 29 that contains information about the lot of test strips. By scanning calibration barcode 29, portable diagnostic device 20 receives the necessary information for calibrating the device for the particular lot of strips being used by the patient. Portable diagnostic device 20 calibrates the testing meter for the particular lot of test strips being used by the patient.

In a preferred embodiment, portable diagnostic device 20 has a communications link for downloading the diagnostic monitoring results and the health related activities that are stored in portable diagnostic device 20. The communications link may be a wireless link or a hard wire connection. The information may be downloaded to a computer associated with the patient and/or the patient's doctor. Periodic reports and graphs could be printed showing the correlations between the diagnostic monitoring results and the patient's health related activities. The information from portable diagnostic device 20 can be analyzed to determine the effect of food, exercise, stress and/or drugs on the patient's health. This analysis may be used to adjust the patient's diet, exercise regimen or drug prescriptions. Further monitoring with portable diagnostic device 20 may determine the effectiveness of these adjustments.

The herein described embodiments of the present invention are intended to provide the preferred embodiments of the present inventions currently contemplated by the applicant. It would be obvious to any one of skill in the relevant art, based on the herein described examples that numerous modifications could be made to the described preferred embodiments without straying from the present invention. Accordingly, the herein described embodiments are merely exemplary in nature and are not intended to represent every possible embodiment of the present invention.

What is claimed is:

1. A portable diagnostic device for use by a user, the portable diagnostic device comprising:
   a) a monitor for measuring diagnostic results of the user;
   b) a scanner for reading a barcode containing information about a health related activity of the user;
   c) a memory for storing said diagnostic results and said information about the health related activity;
   d) a communications link for transmitting said diagnostic results and said information about the health related activity stored in said memory to a remote computer.

2. The portable diagnostic device of claim 1 wherein said diagnostic results relate to a blood sugar level.

3. The system of claim 1 wherein said diagnostic results relate to a blood pressure.

4. The portable diagnostic device of claim 1 wherein said information about the health related activity relates to nutritional information about a food.

5. The portable diagnostic device of claim 1 wherein said information about the health related activity relates to a list of ingredients in a food.

6. The portable diagnostic device of claim 1 wherein said information about the health related activity relates to a type of exercise.

7. The portable diagnostic device of claim 1 wherein said information about the health related activity relates to a type of prescription drug.

8. The portable diagnostic device of claim 1 wherein said memory stores a prescription drug schedule.

9. The portable diagnostic device of claim 8 wherein said information about the health related activity relates to a type of prescription drug and wherein the type of prescription drug is compared to said prescription drug schedule.

10. A system for recording diagnostic results and health related activities of a user, the system comprising:
    a) a portable diagnostic device comprising:
       i) a monitor for measuring a diagnostic result of the user;
       ii) a scanner for reading a barcode containing an identification code;
       iii) a memory for storing said diagnostic result and said identification code;
       iv) a display for displaying a message to said user;
    b) a database containing a plurality of identification codes, each identification code being associated with a health related activity;
    wherein the system determines the health related activity correlated to said identification code read by said scanner and wherein said message displayed to said user relates to said health related activity.

11. The system of claim 10 wherein said diagnostic result relates to a blood sugar level.

12. The system of claim 10 wherein said diagnostic result relates to a blood pressure.

13. The system of claim 10 wherein said health related activity relates to nutritional information about a food.

14. The system of claim 10 wherein said health related activity relates to a list of ingredients in a food.

15. The system of claim 10 wherein said health related activity relates to a type of exercise.

16. The system of claim 10 wherein said health related activity relates to a type of prescription drug.

17. The system of claim 10 wherein said memory stores a prescription drug schedule.

18. The system of claim 17 wherein said health related activity relates to a type of prescription drug and wherein the type of prescription drug is compared to said prescription drug schedule.

19. A method for improved dispensing of a prescription drug to a user, said method comprising the steps of:
    a) providing a portable diagnostic device, said portable diagnostic device having an identification code reader for reading identification codes associated with prescription drugs;
    b) transmitting from a computing station a prescription drug schedule to a communications port of said portable diagnostic device, said prescription drug schedule providing an identification of at least one prescription drug and a set of rules defining when the user should take the prescription drug and when the user should not take the prescription drug;
    c) storing said prescription drug schedule in a memory of said portable diagnostic device;
    d) providing a reminder message on said portable diagnostic device if, according to the set of rules, the user should take the prescription drug;
    e) reading with said portable diagnostic device an identification code associated with a prescription drug;

f) accessing said memory of said portable diagnostic device to determine the set of rules for the prescription drug associated with the identification code read by said portable diagnostic device;

g) providing a warning message on the portable diagnostic device if, according to the set of rules, the user should not take the prescription drug associated with the identification code read by said portable diagnostic device.

20. The method of claim 19 wherein the set of rules is based upon the time of day.

21. The method of claim 19 wherein the set of rules is based upon prescription drugs previously taken by the user.

22. The method of claim 19 wherein the set of rules is based upon food previously eaten by the user.

23. The method of claim 19 wherein the set of rules is based upon a prescribed dosage.

24. The method of claim 19 further including the step of displaying instructions on said portable diagnostic device if the taking of a prescription drug violates the set of rules.

25. The method of claim 19 further including the step of communicating a notification to a remote if the taking of a prescription drug violates the set of rules.

* * * * *